United States Patent
Shaughnessy

(10) Patent No.: US 10,463,334 B2
(45) Date of Patent: Nov. 5, 2019

(54) SYSTEM AND METHOD FOR NON-INVASIVE, QUANTITATIVE MEASUREMENTS OF BLOOD FLOW PARAMETERS IN VASCULAR NETWORKS

(71) Applicant: Wisconsin Alumni Research Foundation, Madison, WI (US)

(72) Inventor: Gabriel Grant Shaughnessy, Nashotah, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 103 days.

(21) Appl. No.: 15/872,457

(22) Filed: Jan. 16, 2018

(65) Prior Publication Data

US 2019/0216417 A1 Jul. 18, 2019

(51) Int. Cl.
| | |
|---|---|
| A61B 6/00 | (2006.01) |
| A61B 5/02 | (2006.01) |
| A61B 5/029 | (2006.01) |
| G01R 33/563 | (2006.01) |
| A61B 5/021 | (2006.01) |
| A61B 5/0285 | (2006.01) |

(52) U.S. Cl.
CPC .............. *A61B 6/504* (2013.01); *A61B 5/029* (2013.01); *A61B 5/02014* (2013.01); *A61B 6/481* (2013.01); *A61B 5/021* (2013.01); *A61B 5/0285* (2013.01); *A61B 6/486* (2013.01); *G01R 33/5635* (2013.01)

(58) Field of Classification Search
CPC ....... A61B 6/504; A61B 6/481; A61B 6/5217; A61B 5/021

USPC ....... 382/128, 130, 131, 132, 133, 134, 170, 382/209; 128/900, 922, 923
See application file for complete search history.

(56) References Cited

U.S. PATENT DOCUMENTS

| | | | |
|---|---|---|---|
| 6,416,741 B1* | 7/2002 | Sutton | A61K 9/1658 424/9.52 |
| 6,643,642 B1 | 11/2003 | Habegger | |
| 8,131,037 B2* | 3/2012 | Inoue | A61B 6/504 382/128 |

(Continued)

OTHER PUBLICATIONS

Davis, et al., "Volumetric limiting spatial resolution analysis of four-dimensional digital subtraction angiography," (2016) Journal of Medical Imaging (Bellingham, Wash.), 3(1), 013503.

(Continued)

*Primary Examiner* — Yosef Kassa
(74) *Attorney, Agent, or Firm* — Quarles & Brady LLP

(57) ABSTRACT

A system and method are provided for generating time resolved series of angiographic volume data having flow information. The system and method are configured to receive angiographic volume data acquired from a subject having received a dose of a contrast agent using an imaging system and process the angiographic volume data to generate angiographic volume images. The angiographic volume data is processed to select a seed vessel in the vessel network, determine a plurality of branch vessels connected to the seed vessel and extending to form a vessel network, determine independent and dependent vessels in the vessel network, apply a flow model to the vessel network, and generate a flow map to be displayed with the angiographic volume images to illustrate time-resolved vascular volumes displaying flow within the vessel network.

18 Claims, 8 Drawing Sheets

(56) References Cited

U.S. PATENT DOCUMENTS

| | | | | |
|---|---|---|---|---|
| 8,265,224 B2* | 9/2012 | Baumgart | ............... | A61B 6/12 |
| | | | | 378/114 |
| 8,553,963 B2* | 10/2013 | Rauch | ...................... | G06T 7/20 |
| | | | | 378/21 |
| 8,643,642 B2 | 2/2014 | Mistretta | | |
| 8,768,031 B2 | 7/2014 | Mistretta | | |
| 8,830,234 B2* | 9/2014 | Mistretta | .................. | A61B 6/02 |
| | | | | 345/419 |
| 8,971,493 B2* | 3/2015 | Zhang | .................. | A61B 5/7285 |
| | | | | 378/150 |
| 9,414,799 B2 | 8/2016 | Mistretta | | |
| 9,626,191 B2* | 4/2017 | Choquette | ............. | G06F 9/3851 |
| 2016/0267704 A1 | 9/2016 | Mistretta | | |

OTHER PUBLICATIONS

Foreman-Mackey, et al. "emcee: The MCMC Hammer," Publ. Astron. Soc. Pac. 125, 306-312 (2013).

Goodman, et al., "Ensemble samplers with affine invariance," Comm. in Applied Mathematics and Computational Science 5, 65-80 (2010).

Shaughnessy, et al., "Quantitative flow and velocity measurements of pulsatile blood flow with 4D-DSA." Proc. SPIE 10132, Medical Imaging 2017: Physics of Medical Imaging, 101325R (Apr. 19, 2017) 1 page.

\* cited by examiner

SYSTEM AND METHOD FOR NON-INVASIVE, QUANTITATIVE MEASUREMENTS OF BLOOD FLOW PARAMETERS IN VASCULAR NETWORKS

STATEMENT REGARDING FEDERALLY SPONSORED RESEARCH OR DEVELOPMENT

This invention was made with government support under HL116567 awarded by the National Institutes of Health. The government has certain rights in the invention.

BACKGROUND

The present disclosure is directed to non-invasive quantitative measurements of blood flow parameters and, in particular, the disclosure relates to a system and method for determining quantitative measurements of blood flow parameters in vascular networks using medical imaging data, such as time-resolved, three-dimensional (3D) angiographic images, referred to as four-dimensional (4D) angiographic x-ray data.

Since the introduction of angiography beginning with the direct carotid artery punctures of Moniz in 1927, there have been ongoing attempts to develop angiographic techniques that provide diagnostic images of the vasculature, while simultaneously reducing the invasiveness associated with the procedure. In the late 1970's, a technique known as digital subtraction angiography (DSA) was developed based on real-time digital processing equipment. Due to steady advancements in both hardware and software, DSA can now provide depictions of the vasculature in both 2D and volumetric 3D formats. Three-dimensional digital subtraction angiography (3D-DSA) has become an important component in the diagnosis and management of people with a large variety of central nervous system vascular diseases as well as other vascular diseases throughout the body.

In recent years competition for traditional DSA has emerged in the form of computed tomography angiography (CTA) and magnetic resonance angiography (MRA). CTA is a less invasive technique but has lower spatial resolution. It is not time-resolved unless the imaging volume is severely limited. The images are not isotropic and secondary reconstruction yields degraded spatial resolution. CTA is also somewhat limited as a standalone diagnostic modality by artifacts caused by bone at the skull base and as well as the contamination of arterial images with opacified venous structures. Further, CTA provides no functionality for guiding or monitoring minimally-invasive endovascular interventions.

Significant advances have been made in both the spatial and the temporal resolution qualities of MRA. Currently, gadolinium-enhanced time-resolved MRA (TRICKS) is widely viewed as a dominant clinical standard for time-resolved MRA. TRICKS enables voxel sizes of about 10 mm$^3$ and a temporal resolution of approximately 10 seconds. Advancements such as HYBRID highly constrained projection reconstruction (HYPR) MRA techniques, which violate the Nyquist theorem by factors approaching 1000, can provide images with sub-millimeter isotropic resolution at frame times just under 1 second. Nonetheless, the spatial and temporal resolution of MRA are not adequate for all imaging situations and its costs are considerable. Furthermore, the spatial and temporal resolution is substantially below other methods, such as DSA.

The recently-introduced, four-dimensional (4D) DSA techniques can use rotational DSA C-arm imaging systems controlled with respect to a particular injection timing so that there is time dependence in the acquired reconstructed 4D volumes. As described in U.S. Pat. No. 8,643,642, which is incorporated herein by reference, a 3D DSA volume can be used as a constraining volume to generate a new 3D volume that contains the temporal information of each projection. As in 3D DSA, a mask rotation without contrast is followed by a second rotation during which contrast is injected. The process creates a series of time resolved 3D angiographic volumes that can be updated, for example, every $\frac{1}{30}$ of a second.

Thus, the above-described systems and methods have improved over time and, thereby, provided clinicians with an improving ability to visualize the anatomy of the vessels being studied. Of course, blood flow through vessels is dynamic and ideally both the dynamics of blood flow and the structural features of the vessels could be used by a clinician to deduce whether or not there was an abnormality. Currently, with ever increasing spatial and temporal resolution, the clinician has been provided with clearer and more accurate information about the geometry (i.e., anatomy) of the vessels. Unfortunately, assessment of the equally important dynamics of blood flow through the vasculature still depends upon a qualitative assessment gained from visualization of a contrast bolus as it passes through the vessels. As such, while the deductions made by the clinician about the structural dynamics and function of the vessel (i.e. anatomy) have correspondingly improved, even the best deductions about the circulatory dynamics (e.g. blood flow and velocity) are still qualitative and thus inherently limited.

As such, many have worked to create systems and methods to derive quantitative measures of complex, in vivo hemodynamics. Some systems rely on interventions to acquire direct quantitative measurements, such as using catheters or the like. Of course, interventional systems and methods are less desirable than non-interventional systems and methods, if the same quality and quantity of information is available.

As such, some have developed systems and methods that use imaging data to derive blood flow measurements. The imaging modalities include ultrasound, MR, 2D DSA, and 4D-DSA. With the advancement of hardware and software in these imaging modalities, some quantitative in vivo blood flow measurements have been made over large 3D volumes in a timely manner. These rich data sets can provide functional information related to the anatomical and hemodynamic properties of complex vessel networks. However, due to the complexity of in vivo blood fluid dynamics, the accurate quantitation of flow parameters is a non-trivial task and has not approached that of interventional systems and methods.

Therefore, it would be desirable to provide systems and methods that simplify the quantitation of hemodynamic parameters, such as flow, area, mean velocity, and the like, in a way that is consistent, repeatable, and understandable to the clinician.

SUMMARY

The present disclosure overcomes the aforementioned drawbacks by providing systems and methods for providing quantitative blood-flow measurements in vascular segments by considering the constraint of blood-flow conservation across a vascular network. The systems and methods provided herein control flow uncertainty to provide quantitative and improved qualitative information on a variety of hemodynamic parameters, thereby, providing clinicians with quantitative information on par with interventional methods.

In accordance with one aspect of the disclosure, a system is provided for generating time resolved series of angiographic volume images having flow or velocity information integrated therewith. The system includes an image processing system configured to receive angiographic volume data acquired from a subject having received a dose of a contrast agent using an imaging system, process the angiographic volume data to generate angiographic volume images. The image processing system is configured to process the angiographic volume data to derive a flow map of blood flow in the angiographic volume images by selecting a seed vessel in the vessel network, determining a plurality of branch vessels connected to the seed vessel and extending to form a vessel network, and determining independent and dependent vessels in the vessel network. The image processing system is further configured to process the angiographic volume data by applying a flow model to the vessel network that enforces flow conservation across the vessel network using the independent and dependent vessels and generating the flow map using the flow model. The system further includes a display configured to display the flow map and the angiographic volume images to illustrate time-resolved vascular volumes displaying flow within the vessel network.

In accordance with another aspect of the disclosure, a method is provided for generating time resolved series of angiographic volume data having blood flow information integrated therewith. The method includes generating a series of 3D time-resolved vascular volumes from time resolved x-ray projection data, selecting a seed vessel to serve as a parent vessel, p, that provides blood flow to daughter vessels, i, j, . . . n, for vessels connected to the seed vessel to form a vessel network, and constructing an adjacency matrix, A, having entries of the form $A_{p,i}$, $A_{p,j}$, . . . $A_{p,n}$. The method further includes identifying daughter vessels that do not have daughter vessels as terminal vessels in the vessel network that have independent degrees of freedom, identifying parent vessels as dependent vessels constructed form the terminal vessels, and enforcing flow conservation through the independent vessels and then the dependent vessels to determine a plurality of flow parameters across the vessel network. The method also includes combining the plurality of flow parameters with the series of 3D time-resolved vascular volumes to encode the flow information in the vascular volumes, and displaying the flow information in the vascular volumes.

The foregoing and other advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Time resolved DSA (4D) volumes are derived from 3D-DSA acquisitions and offer an environment to measure the blood flow and respective measurement uncertainty in a vascular network automatically without user intervention. As will be described, the present disclosure recognizes that vessel segmentation in the static DSA volume allows a mathematical description of the vessel connectivity and flow propagation direction. By constraining the allowable values of flow afforded by the measurement uncertainty and enforcing flow conservation at each junction, a reduction in the effective number of degrees of freedom in the vascular network can be made. This refines the overall measurement uncertainty in each vessel segment and provides a more robust measure of flow. As will be described, experimental results show a 30% reduction in flow uncertainty from a renal arterial case and a 2.5-fold improvement in flow uncertainty in some in vivo vessels. Thus, the systems and methods provided herein provide a quantitative measure of hemodynamics without invasive techniques.

Estimation or quantification of blood flow in specific vessel segments can help diagnose the impact of circulatory disease including stenosis, aneurysms, arterial venous malformations (AVMs), and the like. Moreover, the success of an interventional procedure can be established by increased precision of flow measurements. Small blood flow changes correlated with cardiovascular disease can be better determined if measurement uncertainty is reduced.

As provided herein, as will be described, a full vascular network can be imaged and temporally resolved with 4D-DSA angiographic methods. The vascular network connections can be quantified and combined with segment flow measurements to arrive at refined flow values that both conserve flow and reduce flow measurement uncertainty. This method provides a quantitative approach to treatment planning and evaluation in interventional radiology.

Figure 1:
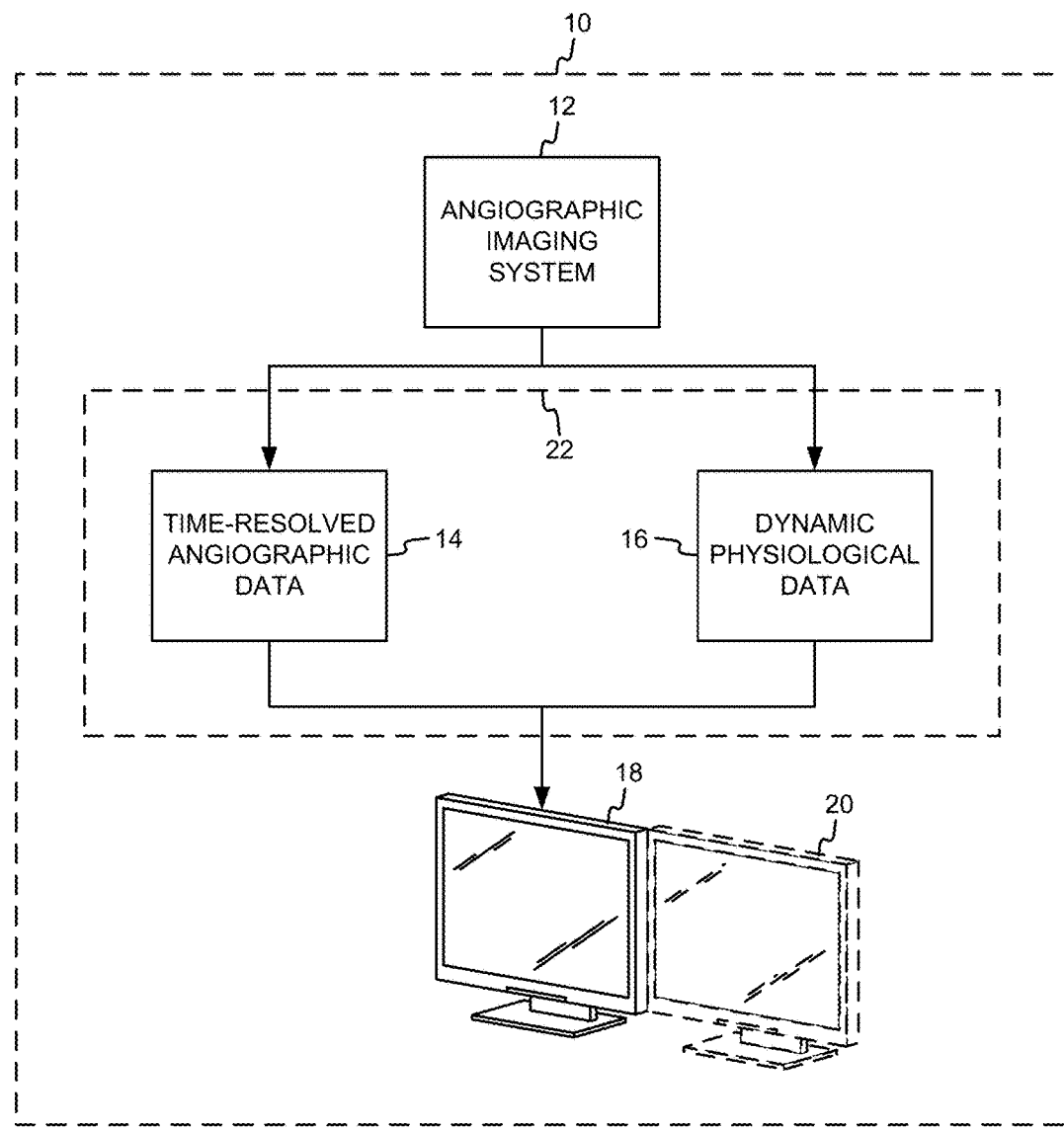
FIG. 1 is a block diagram of a system for creating time-resolved, three-dimensional (3D), angiographic images having dynamic physiological information in accordance with the present disclosure.

Referring to FIG. 1, a system 10 is illustrated for creating time-resolved angiographic images having dynamic physiological information, such as flow or velocity information. In particular, the system 10 includes an angiographic imaging system 12. As will be described, the angiographic imaging system 12 can be used to acquire time-resolved angiographic data 14, from which dynamic physiological information, such as highly-accurate and even quantitative flow or velocity data 16 can be derived. The time-resolved angiographic data 14 and flow or velocity data 16 can be processed and provided to a clinician via a display 18. As will be further described, the information may be provided to the clinician using multiple displays including a first display 18 and a secondary display 20 or multiple additional displays. As will also be described, the process of deriving dynamic physiological information, such velocity or flow data, can be performed partially or in whole using an image processing system, which may include a graphics processing unit (GPU) or other processor, including a central processing unit (CPU) 22.

Figure 2A:
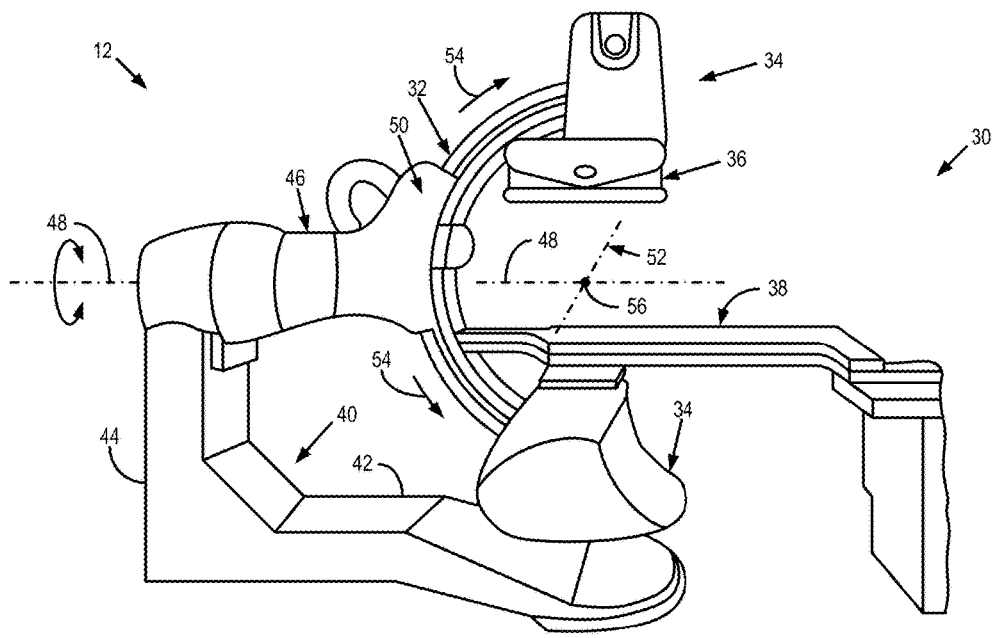
FIG. 2A is a perspective view of an example of an x-ray imaging system that can be used in accordance with the present disclosure to acquire angiographic data.
Figure 2B:
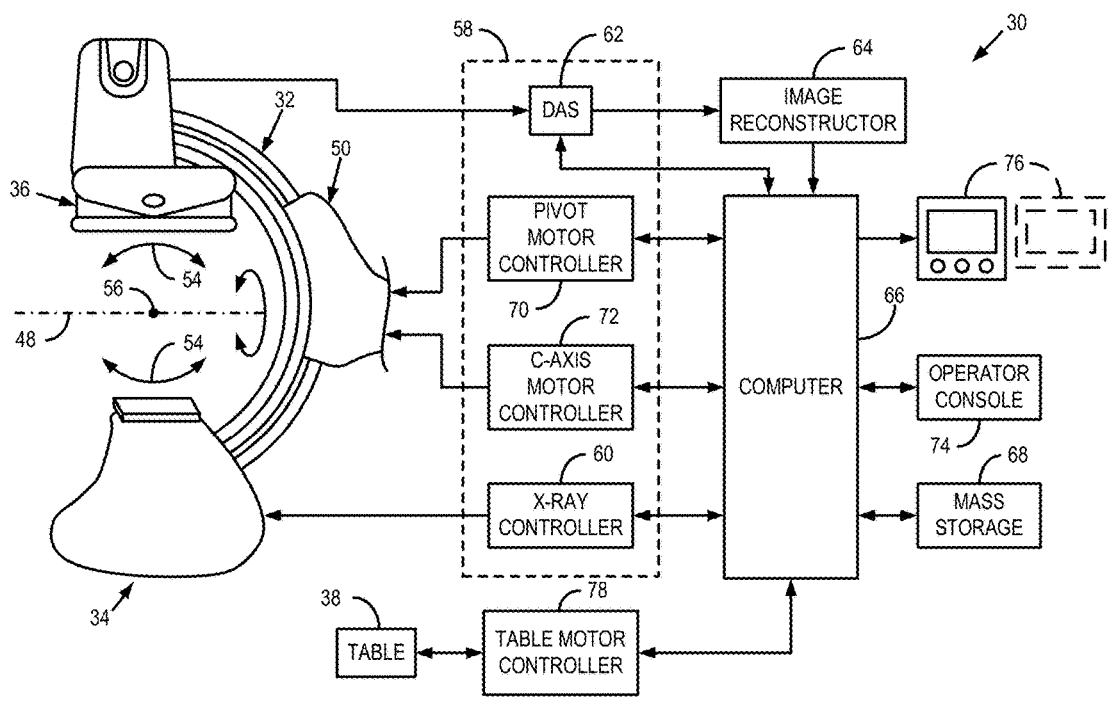
FIG. 2B is a block diagram of the system of FIG. 2A

Referring now to FIGS. 2A and 2B, an example of the angiographic imaging system 12 may include an x-ray imaging system 30. The x-ray imaging system 30 is illustrated as a so-called "C-arm" imaging system; however, other geometries may be used to acquire x-ray angiographic images. For example, any of a variety of x-ray imaging systems capable of acquiring data to create a 4D-DSA image may be used, including systems that acquire time-resolved 2D images using a single plane x-ray system.

The imaging system 30, as illustrated, may be generally designed for use in connection with interventional procedures. The imaging system 30 is characterized by a gantry 32 forming a C-arm that carries an x-ray source assembly 34 on one of its ends and an x-ray detector array assembly 36 at its other end. The gantry 32 enables the x-ray source assembly 34 and detector array assembly 36 to be oriented in different positions and angles around a patient disposed on a table 38, while enabling a physician access to the patient.

The gantry includes a support base 40, which may include an L-shaped pedestal that has a horizontal leg 42 that extends beneath the table 38 and a vertical leg 44 that extends upward at the end of the horizontal leg 42 that is spaced from of the table 38. A support arm 46 is rotatably fastened to the upper end of vertical leg 44 for rotation about a horizontal pivot axis 48. The pivot axis 48 is aligned with the centerline of the table 38 and the support arm 46 extends radially outward from the pivot axis 48 to support a drive assembly 50 on its outer end. The C-arm gantry 32 is slidably fastened to the drive assembly 50 and is coupled to a drive motor (not shown) that slides the C-arm gantry 32 to revolve it about a C-axis 52, as indicated by arrows 54. The pivot axis 48 and C-axis 52 intersect each other at an isocenter 56 that is located above the table 408 and they are perpendicular to each other.

The x-ray source assembly 34 is mounted to one end of the C-arm gantry 32 and the detector array assembly 36 is mounted to its other end. As will be discussed in more detail below, the x-ray source assembly 34 includes an x-ray source (not shown) that emits a beam of x-rays, which are directed at the detector array assembly 36. Both assemblies 34 and 36 extend radially inward to the pivot axis 38 such that the center ray of this cone beam passes through the system isocenter 56. The center ray of the x-ray beam can, thus, be rotated about the system isocenter 56 around either the pivot axis 38, the C-axis 52, or both during the acquisition of x-ray attenuation data from a subject placed on the table 38.

As mentioned above, the x-ray source assembly 34 contains an x-ray source that emits a beam of x-rays when energized. The center ray passes through the system isocenter 56 and impinges on a two-dimensional flat panel digital detector housed in the detector assembly 36. Each detector element produces an electrical signal that represents the intensity of an impinging x-ray and, hence, the attenuation of the x-ray as it passes through the patient. During a scan, the x-ray source and detector array are rotated about the system isocenter 56 to acquire x-ray attenuation projection data from different angles. By way of example, the detector array is able to acquire thirty projections, or views, per second. Generally, the numbers of projections acquired per second is the limiting factor that determines how many views can be acquired for a prescribed scan path and speed.

Accordingly, as will be described, this system or others can be used to acquire data that can be used to crate 4D DSA image data sets that may provide 3D angiographic volumes at the rate of, for example, 30 per second. As will be further described, such 4D DSA images may be augmented with flow or velocity information.

Referring particularly to FIG. 2B, the rotation of the assemblies 34 and 36 and the operation of the x-ray source are governed by a control system 58 of the imaging system 30. The control system 58 includes an x-ray controller 60 that provides power and timing signals to the x-ray source. A data acquisition system (DAS) 62 in the control system 58 samples data from detector elements in the detector array assembly 36 and passes the data to an image reconstructor 64. The image reconstructor 64, receives digitized x-ray data from the DAS 62 and performs image reconstruction. The image reconstructed by the image reconstructor 64 is applied as an input to a computer 66, which stores the image in a mass storage device 68 or processes the image further.

The control system 58 also includes pivot motor controller 70 and a C-axis motor controller 72. In response to motion commands from the computer 66, the motor controllers 70 and 72 provide power to motors in the imaging system 30 that produce the rotations about the pivot axis 38 and C-axis 52, respectively. A program executed by the computer 66 generates motion commands to the motor controllers 70 and 72 to move the assemblies 34 and 36 in a prescribed scan path.

The computer 66 also receives commands and scanning parameters from an operator via a console 74 that has a keyboard and other manually operable controls. An associated display 76 or displays allows the operator to observe the reconstructed image and other data from the computer 66. The operator supplied commands are used by the computer 66 under the direction of stored programs to provide control signals and information to the DAS 62, the x-ray controller 60, and the motor controllers 70 and 72. In addition, the computer 66 operates a table motor controller 78, which controls the patient table 408 to position the patient with respect to the system isocenter 56.

The above-described system can be used to acquire raw angiographic data that can then be processed to generate a time-resolved 3D angiographic image in the form of a 4D DSA image. Referring to FIG. 3, a process for creating a 4D DSA image begins at process block 80 with the acquisition of image data from a region-of-interest in a subject using a medical imaging system, such as a CT system or a single-plane, biplane, or rotational x-ray systems. At process block 82, a time-series of 2D images is generated from at least a portion of the acquired image data. While the time-series of 2D images can have a high temporal and spatial resolution and may include images acquired at different angles around the subject, it generally cannot provide a sophisticated 3D depiction of the subject. At process block 84, a 3D image of the subject is reconstructed from the acquired image data. Though individual projections used to reconstruct this 3D image may themselves convey some degree of temporal information, the reconstructed 3D image itself is substantially free of temporal resolution. For brevity, the 3D image substantially without temporal resolution and the time-series of 2D images may simply be referred to as the "3D image" and "2D images," respectively.

At process block 86, the time-series of 2D images and the static 3D image are selectively combined so that the temporal information included in the 2D images is imparted into the 3D image. This results in the production of a time-resolved 3D image of the subject with high temporal and spatial resolution that is delivered at process block 88. While the selective combination process varies based on the medical imaging system used and the nature of the acquired image data, it generally involves the steps of (1) registering the 2D images to the 3D image, (2) projecting the attenuation value of the pixels in the 2D images into the 3D image, and (3) weighting the 3D image with the projected values for each individual frame of the time-series of 2D images. It is contemplated that the temporal weighting in step (3) generally involves multiplying the projected pixel values with the 3D image. These three steps, which can be referred to as "multiplicative projection processing" (MPP), may be accompanied by additional steps to improve image quality or reduce the prevalence of errors and artifacts. For example, the intensity values of pixels and voxels in the 2D images and 3D image produced at process blocks 82 and 84 may quantify an x-ray attenuation level at a given location in the subject. These attenuation levels may not be preserved when multiplying the 3D image with projected pixel values. Accordingly, more accurate indications of the attenuation levels may be restored using the intensity value at each voxel in the time-resolved 3D image, for example, by taking the n-th root, if (n−1) different sets of 2D images are used, to weight the 3D image.

The 2D images and 3D image produced at process blocks 82 and 84, respectively, can be produced using DSA techniques. That is, 2D images depicting the subject's vasculature can be produced by reconstructing image data acquired as a bolus of contrast passes through the vasculature and subtracting out a pre-contrast, or "mask," image acquired before the administration of contrast agent. Likewise, a 3D image of the same vascular structures can be produced by reconstructing image data acquired as contrast agent occupies the vasculature and subtracting out a mask image to remove signal associated with non-vascular structures. The time-resolved 3D image produced by combining the DSA images depicts the subject's vascular structures with both excellent spatial and excellent temporal resolution and may thus be referred to as a 4D-DSA image. As used herein, this time-resolved 3D image may also be referred to as a 4D image, a 4D angiographic image, or a 4D DSA image. The 4D-DSA images can be displayed as "pure" arterial, pure venous, or composite arterial and venous images and can be fully rotated during each state of the filling of the vasculature, thereby enabling greatly simplified interpretation of vascular dynamics. The spatial resolution of these 4D-DSA images may be on the order of $512^3$ pixels at about 30 frames per second. This represents an increase over traditional 3D-DSA frame rates by a factor between 150 and 600, without a significant image quality penalty being incurred. Further discussion of 4D DSA techniques may be found in U.S. Pat. No. 6,643,642, which is incorporated herein by reference in its entirety. Also, U.S. Pat. No. 8,768,031 is incorporated herein by reference, which extends the 4D DSA imaging process to use time-independent 3D rotational DSA volumes. Furthermore, U.S. Pat. No. 9,414,799, which describes the use of dual-energy x-ray imaging with 4D DSA, is incorporated herein by reference.

Figure 4:
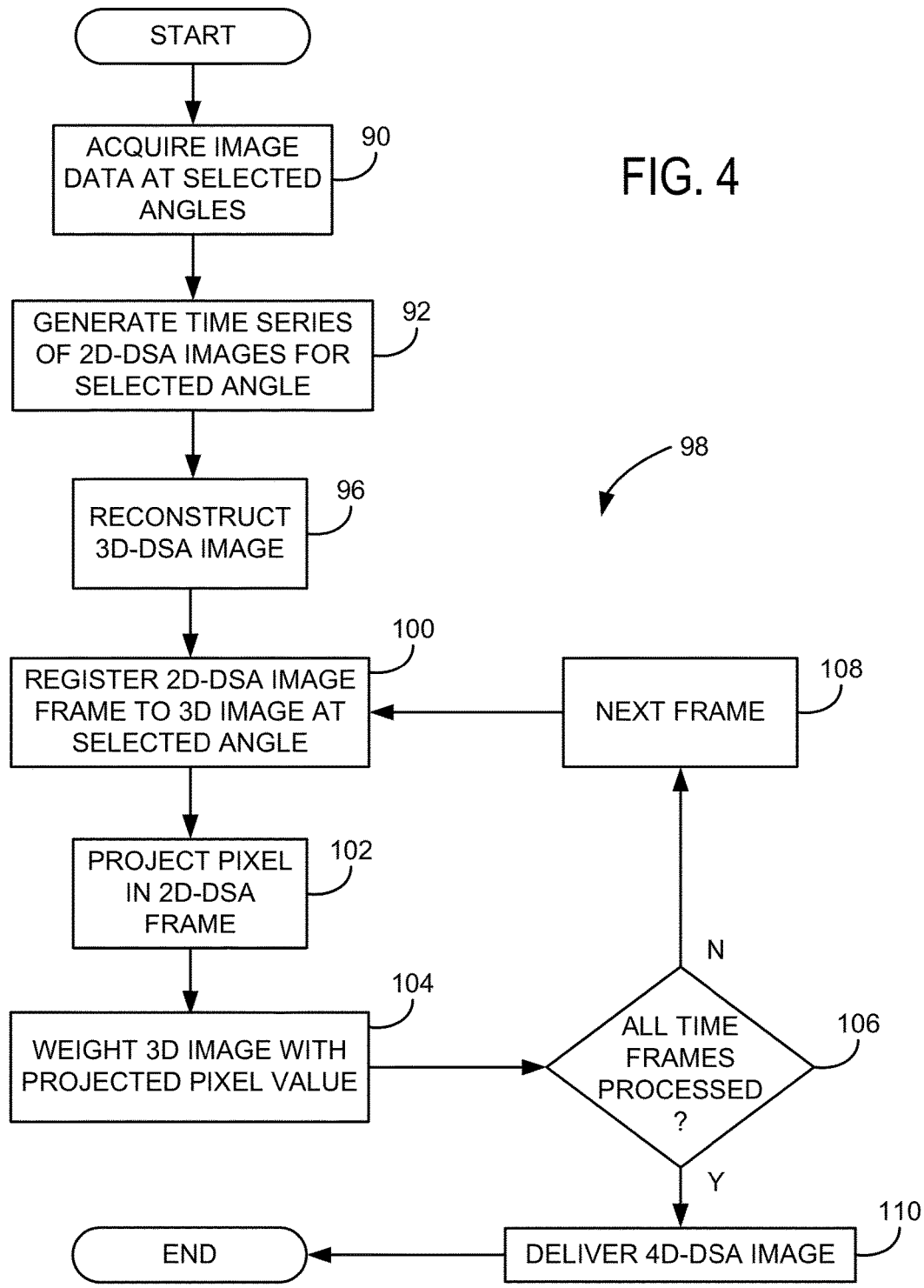
FIG. 4 is a flow chart setting forth further examples of steps for producing a 4D DSA image from x-ray data.

Referring to FIG. 4, a more specific implementation of the above-described process can be employed to produce a 4D-DSA image of a subject using a single-plane x-ray system in combination with a rotational x-ray system or CT system. In this case, the process begins at process block 90, when time-resolved image data from a ROI in the subject is acquired using the single-plane system following the administration of a contrast agent to the subject. Using the above-discussed DSA techniques, a time-series of 2D-DSA images at selected angles about the ROI is generated at process block 92. These 2D-DSA images depict the contrast agent passing through and enhancing arterial structures in the ROI. The 2D-DSA images are substantially free of signal from non-vascular structures, as well as signal from venous structures can be excluded due to the high temporal resolution of the 2D acquisition. A 3D-DSA image is reconstructed at process block 96 from the acquired image data. Specifically, the projections acquired at process block 90 may be log subtracted from those acquired in a non-contrast mask sweep. Typically, vascular structures in the 3D-DSA image are substantially opacified due to the use of contrast agent and the time necessary for data acquisition.

Figure 5:
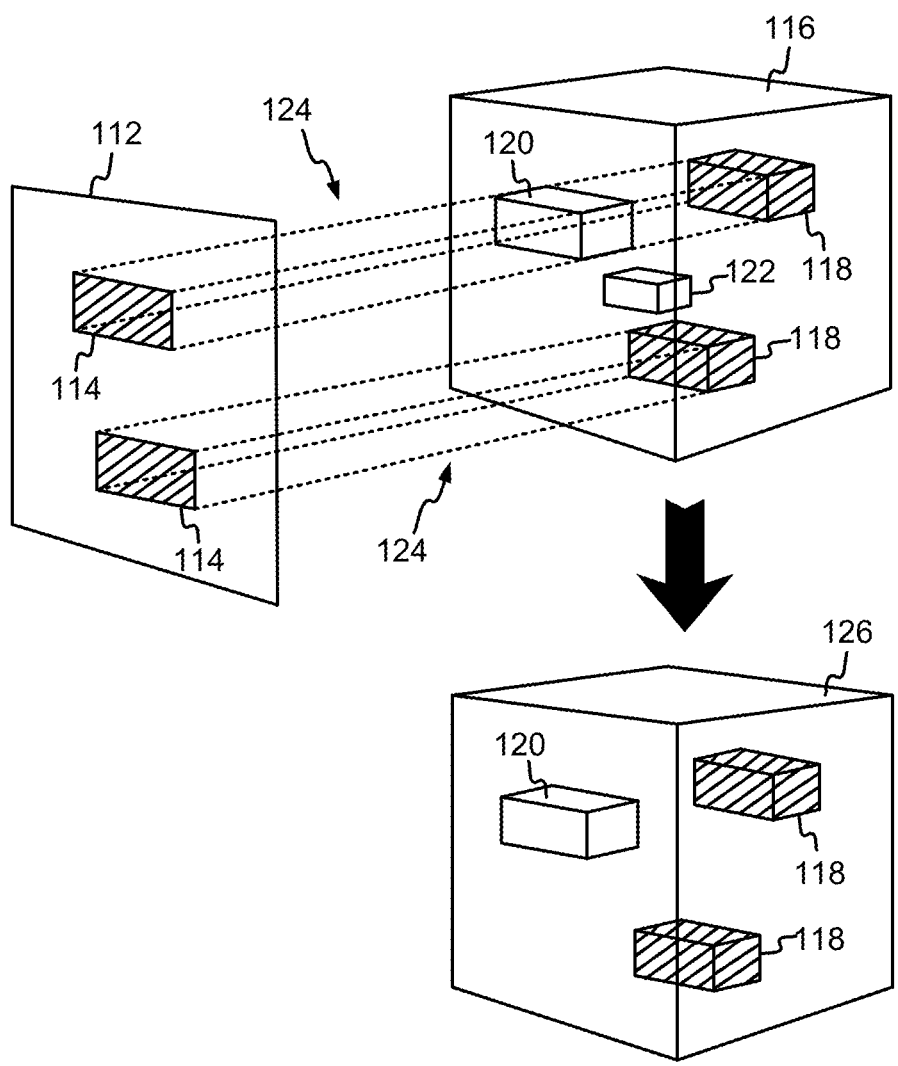
FIG. 5 is a graphic depiction of selective combination of a 3D image with a 2D DSA image frame to produce 4D DSA data.
Figure 6:
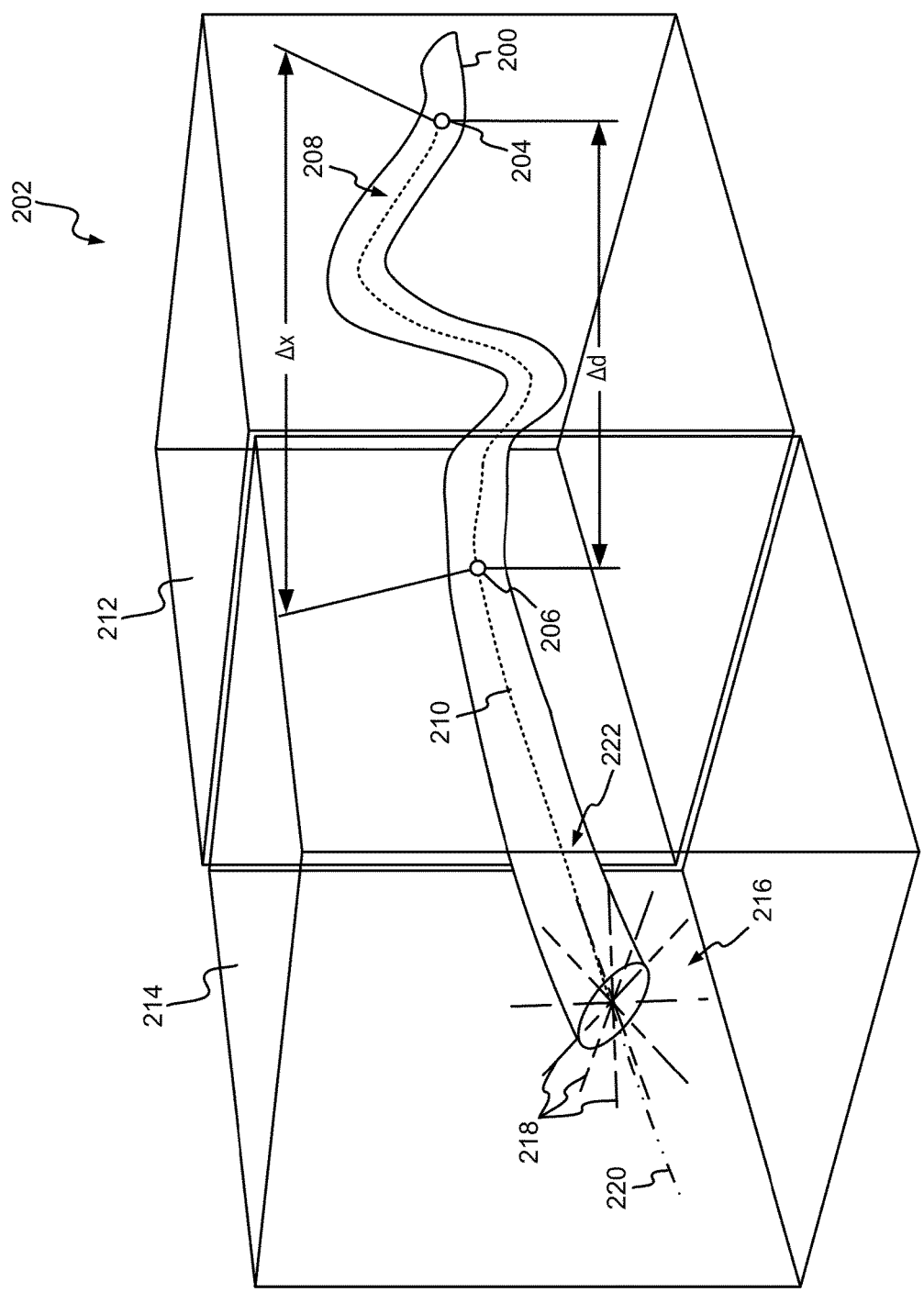
FIG. 6 is a graphic illustration of a vessel taken from a 4D angiographic volume of images.

Referring now to FIGS. 4 and 5, the images produced thus far can be selectively combined with the steps indicated generally at 98 to produce a 4D-DSA image with the detailed 3D resolution of the 3D-DSA image and the temporal resolution of the time-series of 2D-DSA images. In the exemplary depiction of the selective combination process provided in FIG. 5, a single frame of the time-series of 2D-DSA images 112 includes two image regions having arterial signal 114, while the 3D-DSA image 116 includes both arterial signal 118 and venous signal 120 and 122. At process block 100 of FIG. 4, a frame of the 2D-DSA image 112 is registered to the 3D-DSA image 116 at the selected angle and, at process block 102, the values of the pixels in the 2D-DSA frame are projected along a line passing through each respective pixel in a direction perpendicular to the plane of the 2D-DSA frame. The projection of pixels with arterial signal 114 into the 3D-DSA image is indicated generally at 124. For simplicity, the projection of pixels in the 2D-DSA frame with no contrast is not shown. At process block 104 of FIG. 4, the 3D-DSA image 116 is weighted by the values projected from the 2D-DSA frame 112 to produce the 4D-DSA image 126. This may include multiplying the projected values with the voxels of the 3D image that they intersect. The weighting process results in the preservation of the arterial signal 118 and the exclusion, or "zeroing-out," of undesired venous signal 122 in the 4D-DSA image. In addition, the intensity value of the arterial signal 114 in the 2D-DSA frame is imparted into the 3D arterial signal volume 118, thereby allowing the changes in arterial signal over time captured by the 2D-DSA images to be characterized in the 4D-DSA image. At decision block 106 of FIG. 4, if all of the frames have yet to be processed, the process moves to the next frame of the time-series of 2D-DSA images at process block 108 and repeats the selective combination process generally designated at 98. This cycle continues until, at decision block 106, it is determined that a 4D-DSA image has been generated for all relevant time frames. The 4D-DSA image can thus be delivered at process block 110.

The venous signal 120 preserved in the 4D-DSA image 126 illustrates a potential challenge when generating 4D images using only a single time-series of 2D images acquired at a single angle. That is, signal from desired structures, such as the arterial signal 114 in this example, can inadvertently be deposited in 3D voxels representing undesired structures, such as the venous region 120 in this example. The unwanted structures can thus be preserved in the 4D image as "shadow artifacts" when their signal lies along the projected values of a desired structure in a dimension inadequately characterized by the time-series of 2D images. This can result, for example, in a 4D-DSA image in which desired arterial structures are obscured by undesired venous structures for some time frames. However, this will cause a temporary anomaly in the contrast versus time course for the vein. If the time frames of the 4D-DSA image are analyzed, this anomaly can be recognized as inconsistent with the general waveform of the vein and the vein can be suppressed in the time frame where the projected arterial signal is strong. Accordingly, temporal parameters such as mean transit time (MTT) or time-to-fractional-peak can be calculated for each voxel and this information can be used to clean up shadow artifacts. To assist an operator in identifying shadow artifacts and temporal irregularities, the temporal parameters can be color-coded and superimposed on the 4D-DSA image delivered at process block 110 of FIG. 4. The temporal parameters can also be exploited to infer information related to potential perfusion abnormalities in the absence of direct perfusion information from parenchymal signal. Further still and as will be described in detail, dynamic physiological information, such as velocity information, can be determined from the acquired data.

The acquisition of contrast enhanced image data can be performed following the administration of contrast agent to the subject via either IV or IA injection. When scanning a local area, IA injections allow high image quality and temporal resolution as well as reduced contrast agent dose. However, IV injections are often more suitable for scanning larger regions where multiple IA injections at different locations and different arteries would otherwise be required.

Regardless of whether the contrast agent is introduced as an IV or IA injection, systems and methods for utilizing information about the time of arrival (TOA) of the contrast agent can be used to provide flow or velocity data along with the 4D DSA images. For example, co-pending U.S. patent application Ser. No. 14/643,853, filed Mar. 10, 2015, and published as US Patent Application Publication No. 2016/0267704, describes such a system and method and is incorporated herein by reference in its entirety. These systems and methods can be used to acquire data that, in accordance with the present disclosure, can be used to determine blood velocity and flow.

As will be described, the present disclosure provides a system and method that can deliver 4D DSA images including information about dynamic physiological characteristics of the structures that are spatially and temporally resolved in the 4D DSA images. That is, while 4D DSA images, by definition, are spatially resolved in three dimensions and also temporally resolved, the present disclosure provides systems and methods to provide further information to a clinician that can be coupled with the 4D DSA images, for example, to communicate blood flow, volume, velocity, or other information within the 4D DSA images. Furthermore, the present disclosure can derive information about the dynamic physiological characteristics, such as flow direction, flow volume, or velocity, from the 4D DSA data with great accuracy and even quantitatively.

Specifically, referring again to FIG. 3, at process block 128 a seed vessel of a vascular network is selected using the images. The seed vessel may be chosen either automatically or manually. If selected automatically, as one non-limiting example, the vessel with the largest measured flow may be selected. At process block 130, the system follows the flow paths extending from the selected vessel. That is, whether selected automatically or manually, the selected vessel is treated as a "parent" to determine subsequent vessels that receive blood flow from the parent, such that a "vascular network" is traversed according to the connecting vessels.

With the down-flow or subsequent paths from the parent vessel determined, at process block 132 an adjacency matrix, A, is constructed to model the vessel network. Consider a parent vessel, p, that flows into two daughter vessels, i and j. The entries of A are populated as $A_{p,i}=1$ and $A_{p,j}=1$. The final adjacency matrix is created after the entire vessel network is traversed. Note that, by construction, the entries of A are not necessarily symmetric. That is to say, the adjacency matrix is directed. For example, in the vessel network illustrated in FIG. 7, the adjacency matrix is given by:

$$A_{i,j} = \begin{pmatrix} 0 & 1 & 1 & 0 & 0 & 0 & 0 & 0 & 0 \\ 0 & 0 & 0 & 1 & 1 & 0 & 0 & 0 & 0 \\ 0 & 0 & 0 & 0 & 0 & 1 & 1 & 0 & 0 \\ 0 & 0 & 0 & 0 & 0 & 0 & 0 & 0 & 0 \\ 0 & 0 & 0 & 0 & 0 & 0 & 0 & 0 & 0 \\ 0 & 0 & 0 & 0 & 0 & 0 & 0 & 1 & 1 \\ 0 & 0 & 0 & 0 & 0 & 0 & 0 & 0 & 0 \\ 0 & 0 & 0 & 0 & 0 & 0 & 0 & 0 & 0 \\ 0 & 0 & 0 & 0 & 0 & 0 & 0 & 0 & 0 \end{pmatrix} \quad (1)$$

Figure 7:
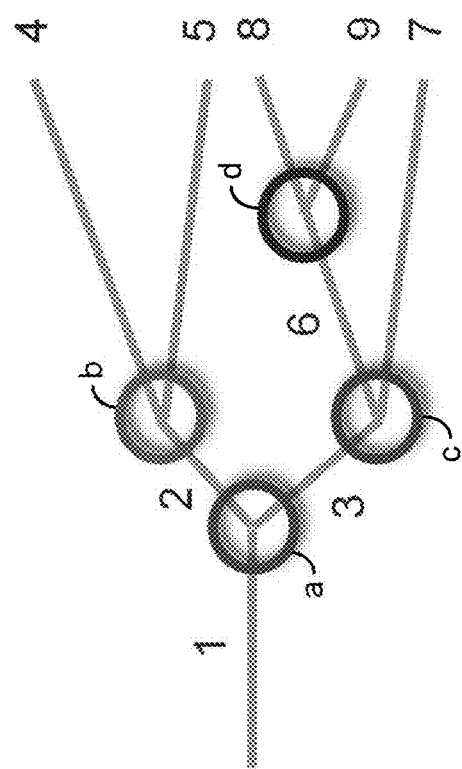
FIG. 7 is a schematic illustration of vessels and junctions for analysis in accordance with the systems and methods of the present disclosure.

That is, FIG. 7 is a graphical representation of a bifurcating vascular network. Branches or vessel segments are numbered 1-9 and the junctions are labeled "a" through "d." Junction "a" is reflected by the "1's" in columns two and three in the matrix. Junction "b" is reflected by the "1's" in columns four and five in the matrix. Junction "c" is reflected in columns six and seven of the matrix, and junction "d" is reflected by the "1's" in columns eight and nine in the matrix.

In this network, there are 5 terminal branches that serve as the independent degrees of freedom of the vascular system, while all other branches have flows that can be constructed from this independent set. Thus, at process block 134, the vessels are processed to determine independent and dependent vessels. Specifically, for a vector of flows enumerated by their respective vessel number, $F_i$, the terminal branches can readily be identified as not being a parent vessel in the construction of A. These terminal branches are then identified by index i, when $\Sigma_j A_{ij}=0$. Even if flow in these terminal branches is not quantitatively measured, they nevertheless have connectivity to the vascular network and can naturally serve as independent degrees of freedom. These independent vessels are noted collectively as I, while the complementary vessels that are the dependent degrees of freedom (i.e. are parents to some vessel) are denoted as D.

With this construct in place, the present disclosure recognizes that flow conservation can be enforced. That is, at process block 136, flow conservation is enforced throughout the vascular network. In one non-limiting example, flow conservation can be enforced through the independent vessels and then the dependent vessels. For the independent vessels, this can be done by filling a vector F with only flows from I:

$$F^I = \begin{cases} F_i & \text{for } i \text{ in } I \\ 0 & \text{otherwise} \end{cases}, ; \quad (2)$$

where $F_i$ is the flow in branch i. Then, for flow conservation enforced on the parents of terminal branches, this can be achieved by applying:

$$F = A \square F^I \quad (3).$$

Thus, this construct is repeated to let the information of flows at the terminal vessels to propagate toward the proximal branches. The number of times that the process repeats is equal to the depth of the vessel network, d, or the number of vessels between the selected seed vessel from process block 128 and the last terminal vessel. Thus, at process block 136, the flow of the entire network can be found in terms of the independent degrees of freedom, $F^I$ by:

$$F = A^d \square F^I \quad (4).$$

Figure 3A:
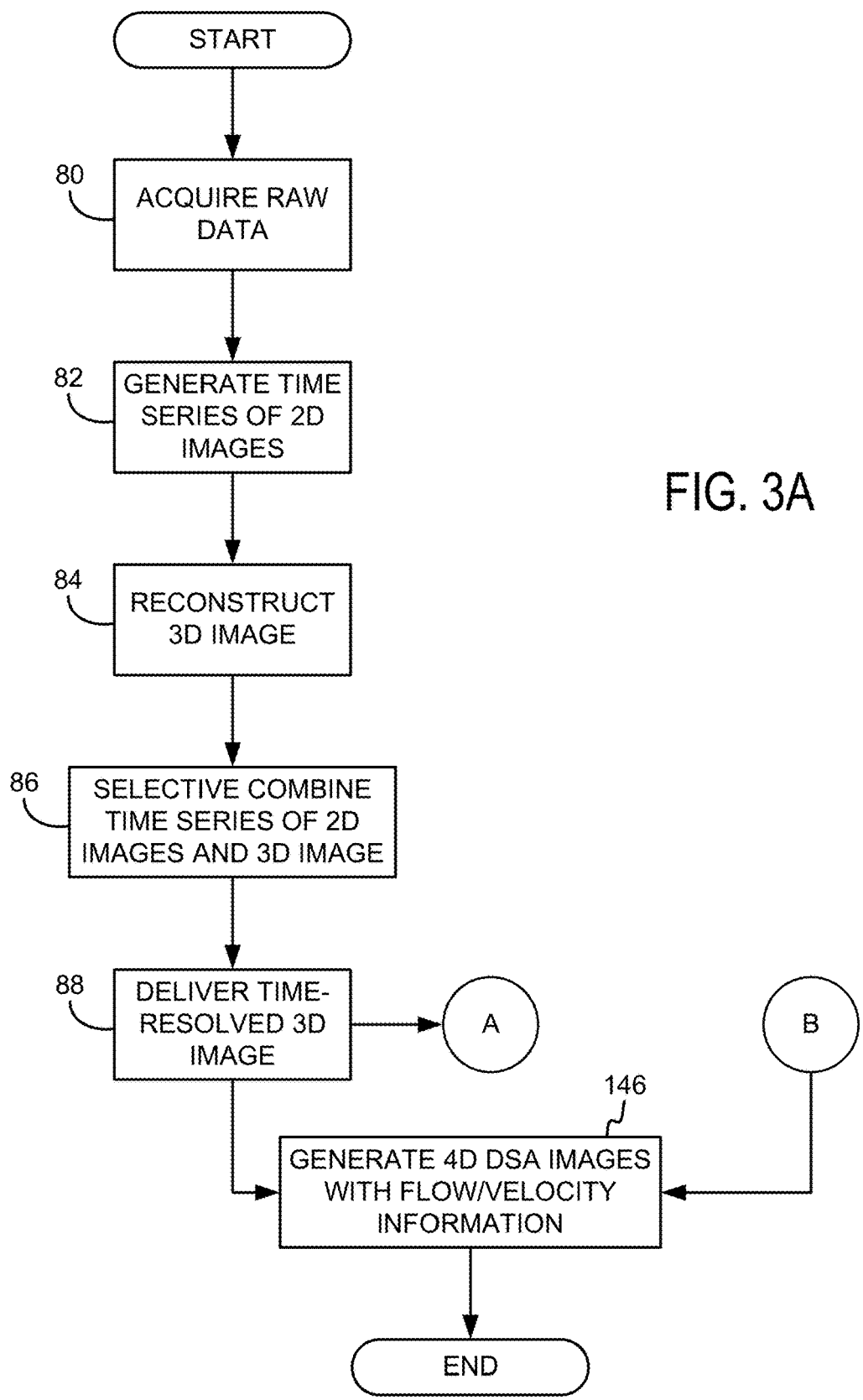
FIG. 3A is a flow chart setting forth examples of steps for producing a 4D DSA image including flow information in accordance with the present disclosure.

With these steps completed, a complete set of flows in a vascular network is formed that has, as an input, the set of independent degrees of freedom and an adherence to flow conservation at each junction and a flow map can be generated at process block 144, which is then combined with the images described above to create the 4D DSA images with flow, volume, velocity, or other hemodynamic information at process block 146 of FIG. 3A, such as by color coding or the like. The function that performs this operation is denoted as:

$$G(F^I) = F \quad (5).$$

Figure 3B:
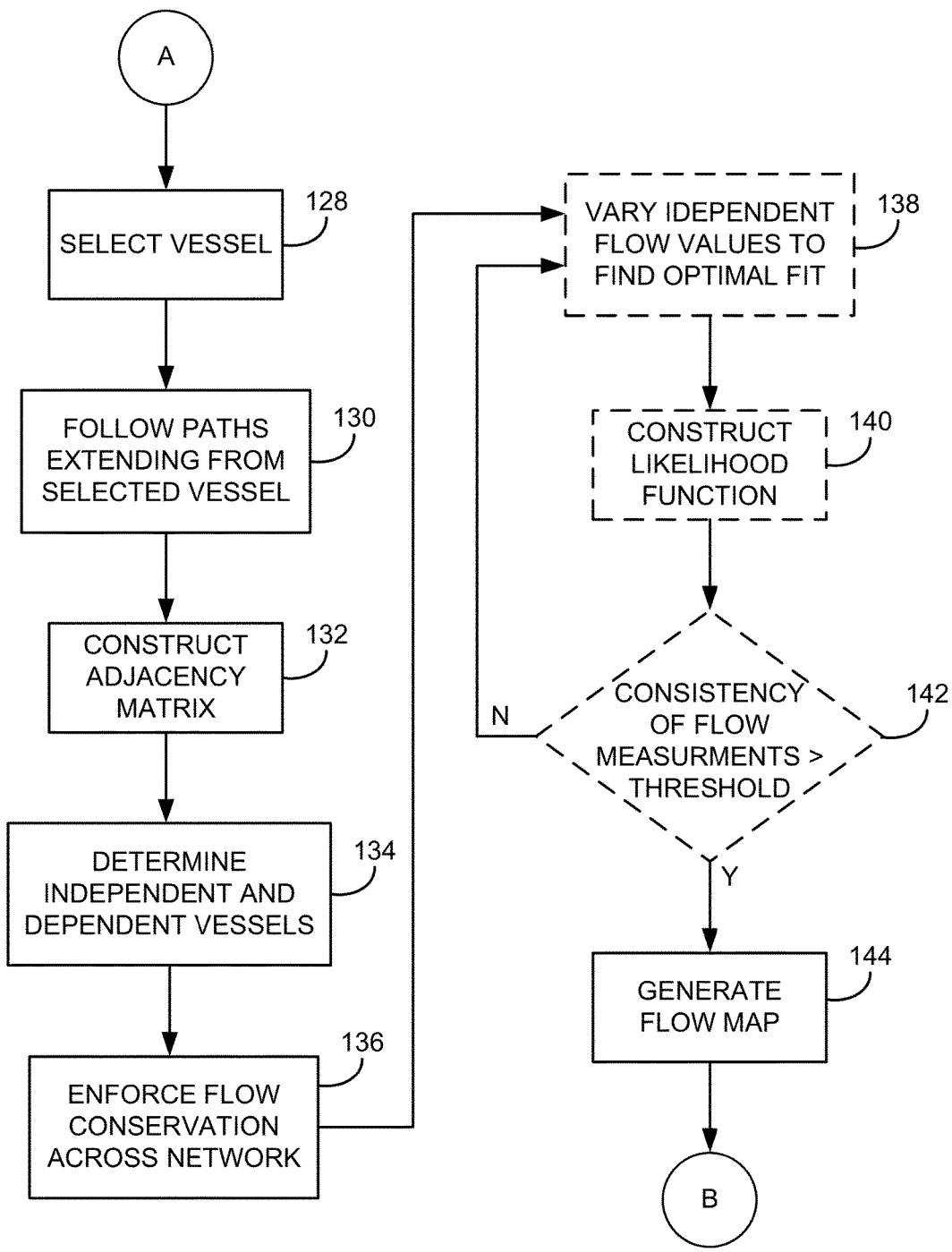
FIG. 3B is a continuation of the flow chart of FIG. 3A.

Continuing with respect to FIG. 3B, to give a more complete picture of the vascular network subject to both the flow measurements and flow conservation, optional inference of flow measurements can be performed. Specifically, at process block 138 the independent flow values can be varied to discern an optimal fit of the flow conservation model subject to the vascular network flow data.

As one non-limiting example, a Bayesian analysis can be used to perform the analysis of the inference of flow measurements. Specifically, as one particular non-limiting example, a Markov Chain Monte Carlo (MCMC) model can be used to fit the available data. The MCMC approach has foundations on Bayesian methods to scan over specified input parameters given available data. In Bayes' rule, the posterior probability of the model parameters, x, given data, q, and model, M, is given by:

$$p(x|q, M) = \frac{\pi(x|M) p(q|x, M)}{p(q|M)}; \quad (6)$$

where $\pi(x|M)$ is prior on the model parameters that contains information on the parameters before unveiling the data. The p(q|x, M) term is the likelihood and is given below in Eq. 8. The p(q|M) term is called the evidence, but can safely be ignored when using the MCMC, since probabilities are properly normalized to unity. That is, MCMCs have desirable characteristics when fitting models to data. It is much more efficient at sampling the parameter space than grid search methods, especially in models with higher dimensionality (i.e. larger number of vessels).

Typically, the MCMC begins with a random point in parameter space. This point, $x_0$, seeds a series of points that make up a chain whereupon the meaningful statistical information can be extracted. To form this chain, another point, $x_{trail}$, in parameter space is randomly selected as a trial point. The next point in the chain, $x_{i+1}$, is assigned via the criteria:

$$x_{i+1} = \begin{cases} x_i & \text{if } \frac{\mathcal{L}(x_{trial})}{\mathcal{L} x_i} < X \\ x_{trial} & \text{if } \frac{\mathcal{L}(x_{trial})}{\mathcal{L} x_i} > 1 \end{cases}; \quad (7)$$

for some $0 \leq X \leq 1$ that is a uniform random value. This process repeats many times and as the number of iterations increases, the collection of points in parameter space asymptotes to the posterior probability distribution of the flows given the flow conservation model. In addition, the set formed by any continuous function of the points in the chain, $f(x_i)$, also follows the posterior distribution of that function of the parameters given the data.

In order to estimate the consistency of flow measurements throughout a vascular network subject to flow conservation, a likelihood function is constructed at process block 140 to account for the deviation of flow with respect to the measured flow and uncertainty. The log likelihood is taken to be:

$$\text{Log}\mathcal{L} = -\frac{1}{2} \sum \frac{(F - G(F^I))^2}{\delta F^2}; \quad (8)$$

where $\delta F$ is the measurement uncertainty estimated for each vessel's flow and the sum runs over all vessels in the network.

One example of a Bayesian method that can be used to fit the model to data is an Affine-Invariant Ensemble (AIE) variety of the MCMC algorithms. Some examples of such methods are described in Goodman, J. and Weare, J., "Ensemble samplers with affine invariance," Comm. in Applied Mathematics and Computational Science 5, 65-80 (2010). And Foreman-Mackey, D., Hogg, D. W., Lang, D., and Goodman, J., "emcee: The MCMC Hammer," Publ. Astron. Soc. Pac. 125, 306-312 (2013), both of which are incorporated herein by reference in their entirety.

The AIE-MCMC model extends the usual MCMC approaches by considering a series of parallel chains called "walkers". A trial point is taken to be a random location along a line con-joining two randomly selected walkers in the chain. This property greatly speeds up the efficiency over the basic MCMC algorithm. A collection of randomly chosen "walkers" at time, $t, \{x_i(t)\}$, are placed in parameter space. A given walker's next trial position, $x_i(t)'$, is chosen along a line connecting it to another randomly chosen walker, $x_j$, with the trial:

$$x_i(t) \rightarrow x'_i = x_j + Z(x_i(t) - x_j) \quad (9);$$

where Z is a random variable with the distribution:

$$g(z) \propto \frac{1}{\sqrt{z}}; \quad (10)$$

in the interval [1=a; I] and vanishes elsewhere. A given trial point (p) is accepted if:

$$p \equiv z^{N-1} \frac{\mathcal{L}_{t+1}}{\mathcal{L}_t} > r; \quad (11)$$

where r is a uniform random variate. This selection ensures detailed balance within the algorithm, which is desirable for the algorithm to preserve statistically relevant quantities like the posterior probability distribution.

The parameter a sets the scale of jumps. The value a=2 is often used because it yields a very efficient exploration of the parameter space.

A "burn-in" period can be allowed to prevent bias from the correlation of the walker's initial random state to the set of walkers used for the posterior distribution. This is guaranteed by constructing the autocorrelation time:

$$C_i(T) = \frac{1}{n-T}\sum_{t=1}^{n-T}(x_i(t)-\bar{x}_i)(x_i(t+T)-\bar{x}_i); \quad (12)$$

for each input parameter and verify that the burn-in length is greater than the lag T where $C_i(T)<0:1$, or there is at most, for example, a 10% correlation between the initial random state to the state that begins the chain in any of the independent variables of interest.

Thus, for each vessel junction, flow conservation is maintained, which provides accurate, reproducible, and quantitative flow parameters. With respect to individual flow uncertainty, the systems and methods described above can be used to test each junction automatically for anomalous flow measurements, recover missing flow measurements from a poor phase fit, and/or improve overall flow measurements of the broader system. Thus, the above-described systems and methods can be used to identified missing branches or mis-measured flows from pre-existing information.

The combination of quantitative and qualitative blood flow information can be used to provide a more complete understanding of cardiovascular diseases. 4D-DSA using C-Arm angiographic methods can be used to provide data that, as described above, can provide a temporally-resolved, full-vascular network maps with flow information embedded in the contrast dynamics. The vascular network connections can be quantified and combined with segment flow measurements to arrive at refined flow values that both conserve flow and reduce flow measurement uncertainty. The majority of vessel networks have similar branching structures readily conform to the general description provided above. Furthermore, the techniques provided herein to be readily adapted for use throughout the body (cardiac, hepatic, renal, and the like) with other imaging modalities, such as traditional MRI, ultrasound, and other modalities that can derive flow information. The identification of abnormal flow conservation is highlighted by the use of this technique and can aid in the quick localization of potential diseased vessel segments. This method provides a quantitative approach to treatment planning and evaluation in interventional radiology.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for generating time resolved series of angiographic volume images having flow or velocity information integrated therewith, the system comprising:
an image processing system configured to:
receive angiographic volume data acquired from a subject having received a dose of a contrast agent using an imaging system;
process the angiographic volume data to generate angiographic volume images;
process the angiographic volume data to derive a flow map of blood flow in the angiographic volume images by:
selecting a seed vessel in the vessel network;
determining a plurality of branch vessels connected to the seed vessel and extending to form a vessel network;
determining independent and dependent vessels in the vessel network;
applying a flow model to the vessel network that enforces flow conservation across the vessel network using the independent and dependent vessels;
generating the flow map using the flow model; and
a display configured to display the flow map and the angiographic volume images to illustrate time-resolved vascular volumes displaying flow within the vessel network.

2. The system of claim 1 wherein the image processing system is configured to assemble an adjacency matrix to determine the independent and dependent vessels in the vessel network.

3. The system of claim 2 wherein the flow model enforces flow conservation by filling a vector, F, with only flows from independent vessels, I, as $$F^I = \begin{cases} F_i & \text{for } i \text{ in } I \\ 0 & \text{otherwise} \end{cases},$$

where $F_i$ is flow in a given branch of the independent vessel i and then enforcing flow conservation on terminal branches of dependent vessels by applying $F=A\square F^I$, where A is the adjacency matrix.

4. The system of claim 1 wherein the image processing system is configured to generate the flow map by creating a complete set of flows in the vessel network by determining an input to the vessel network and a set of independent degrees of freedom, and applying the flow model to apply flow conservation at each junction in the vessel network.

5. The system of claim 1 wherein the image processing system is configured to assess flow values across the vessel network for consistency of flow measurements within a tolerance threshold before generating the flow map.

6. The system of claim 1 wherein the flow model is implemented using Markov Chain Monte Carlo (MCMC) model.

7. The system of claim 1 wherein angiographic volume data includes x-ray projection data.

8. The system of claim 7 wherein the x-ray projection data includes four-dimensional (4D) digital subtraction angiography data.

9. The system of claim 1 wherein the display is configured to illustrate the at least one of the flow direction, flow volume or flow velocity of flow within the vessel network.

10. The system of claim 9 wherein the display is configured to show a quantitative value of the at least one of the flow direction, flow volume or flow velocity of flow within the vessel network.

11. The system of claim 1 wherein the image processing system is further configured to:
use the seed vessel as a parent vessel, p, that provides blood flow to daughter vessels, i, j, . . . n, for vessels connected to the seed vessel to form the vessel network;
construct an adjacency matrix, A, having entries of the form $A_{p,i}, A_{p,j}, \ldots A_{p,n}$;
identify daughter vessels that do not have daughter vessels as terminal vessels in the vessel network that have independent degrees of freedom;
identify parent vessels as dependent vessels constructed form the terminal vessels;

enforce flow conservation using the flow model through the independent vessels and then the dependent vessels to generate the flow map.

12. A method for generating time resolved series of angiographic volume data having blood flow information integrated therewith, the method including steps comprising:
    generating a series of 3D time-resolved vascular volumes from time resolved x-ray projection data;
    selecting a seed vessel to serve as a parent vessel, p, that provides blood flow to daughter vessels, i, j, . . . n, for vessels connected to the seed vessel to form a vessel network;
    constructing an adjacency matrix, A, having entries of the form $A_{p,i}$, $A_{p,j}$, . . . $A_{p,n}$;
    identifying daughter vessels that do not have daughter vessels as terminal vessels in the vessel network that have independent degrees of freedom;
    identifying parent vessels as dependent vessels constructed form the terminal vessels;
    enforcing flow conservation through the independent vessels and then the dependent vessels to determine a plurality of flow parameters across the vessel network;
    combining the plurality of flow parameters with the series of 3D time-resolved vascular volumes to encode the flow information in the vascular volumes; and
    displaying the flow information in the vascular volumes.

13. The method of claim 12 wherein enforcing flow conservation includes filling a vector, F, with only flows from independent vessels, I, as $$F^I = \begin{cases} F_i & \text{for } i \text{ in } I \\ 0 & \text{otherwise} \end{cases},$$

where $F_i$ is flow in a given branch of the independent vessels i and then enforcing flow conservation on terminal branches of dependent vessels by applying $F = A \square F^I$, where A is the adjacency matrix.

14. The method of claim 12 wherein all steps are automatically performed by a computer system.

15. The method of claim 12 further comprising assessing low values across the vessel network for a consistency of flow measurements to determine a consistency within a tolerance threshold before determining the flow parameters.

16. The method of claim 12 further comprising using Markov Chain Monte Carlo (MCMC) model to enforce the flow conservation.

17. The method of claim 12 wherein the time resolved x-ray projection data includes four-dimensional (4D) digital subtraction angiography data.

18. The method of claim 12 wherein the displaying includes displaying quantitative values of at least one of the flow direction, flow volume, or flow velocity of flow within the vessel network.

* * * * *

UNITED STATES PATENT AND TRADEMARK OFFICE
CERTIFICATE OF CORRECTION

PATENT NO. : 10,463,334 B2
APPLICATION NO. : 15/872457
DATED : November 5, 2019
INVENTOR(S) : Gabriel Grant Shaughnessy It is certified that error appears in the above-identified patent and that said Letters Patent is hereby corrected as shown below:

In the Specification

Column 10, Line 65, Eq. (3), "$F = A \square F^T$" should be -- $F = A \cdot F^T$ --.

Column 11, Line 7, Eq. (4), "$F = A^d \square F^T$" should be -- $F = A^d \cdot F^T$ --.

Signed and Sealed this
Eleventh Day of February, 2020

Andrei Iancu
*Director of the United States Patent and Trademark Office*